United States Patent [19]
Breit

[11] Patent Number: 5,998,788
[45] Date of Patent: Dec. 7, 1999

[54] ION MOBILITY SPECTROMETER

[75] Inventor: Ulrich Breit, Munich, Germany

[73] Assignee: LFK-Lenkflugkoerpersysteme, Germany

[21] Appl. No.: 08/986,800

[22] Filed: Dec. 8, 1997

[30] Foreign Application Priority Data

Dec. 6, 1996 [DE] Germany .................. 196 50 612

[51] Int. Cl.⁶ ............................................ H01J 49/40
[52] U.S. Cl. ................................ 250/286; 250/287
[58] Field of Search .............................. 250/286, 287

[56] References Cited

U.S. PATENT DOCUMENTS

| | | | |
|---|---|---|---|
| 4,390,784 | 6/1983 | Browning et al. | 250/287 |
| 4,633,083 | 12/1986 | Knorr et al. | 250/282 |
| 5,789,745 | 8/1998 | Martin et al. | 250/286 |
| 5,834,771 | 11/1998 | Yoon et al. | 250/286 |

FOREIGN PATENT DOCUMENTS

| | | | |
|---|---|---|---|
| 41 34 212 A1 | 4/1993 | Germany | G01N 27/62 |
| 195 13 459 A1 | 1/1996 | Germany | H01J 49/40 |

*Primary Examiner*—Edward P. Westin
*Assistant Examiner*—Nikita Wells
*Attorney, Agent, or Firm*—Evenson, McKeown, Edwards & Lenahan, P.L.L.C.

[57] ABSTRACT

In an ion mobility spectrometer (IMS), the essential parts, namely the ion gate, the drift chamber, and the ion collector, consist of pieces that are slice or wafer shaped, and are either anisotropically etchable or can be machined using micro-mechanical methods. The parts are held together by clamps, adhesives, or other known assembly methods. The drift chamber consists of two sliced pieces with a through groove being etched or milled in one of them. The groove is covered by the other smooth piece so that a drift channel is produced. The drift channel is closed at one end by a grid-shaped ion gate, which is similarly made from a sliced piece by etching or milling while the opposite end of the drift channel is closed by the ion collector, which is likewise made from a sliced piece that is electrically conducting on the inside.

14 Claims, 1 Drawing Sheet

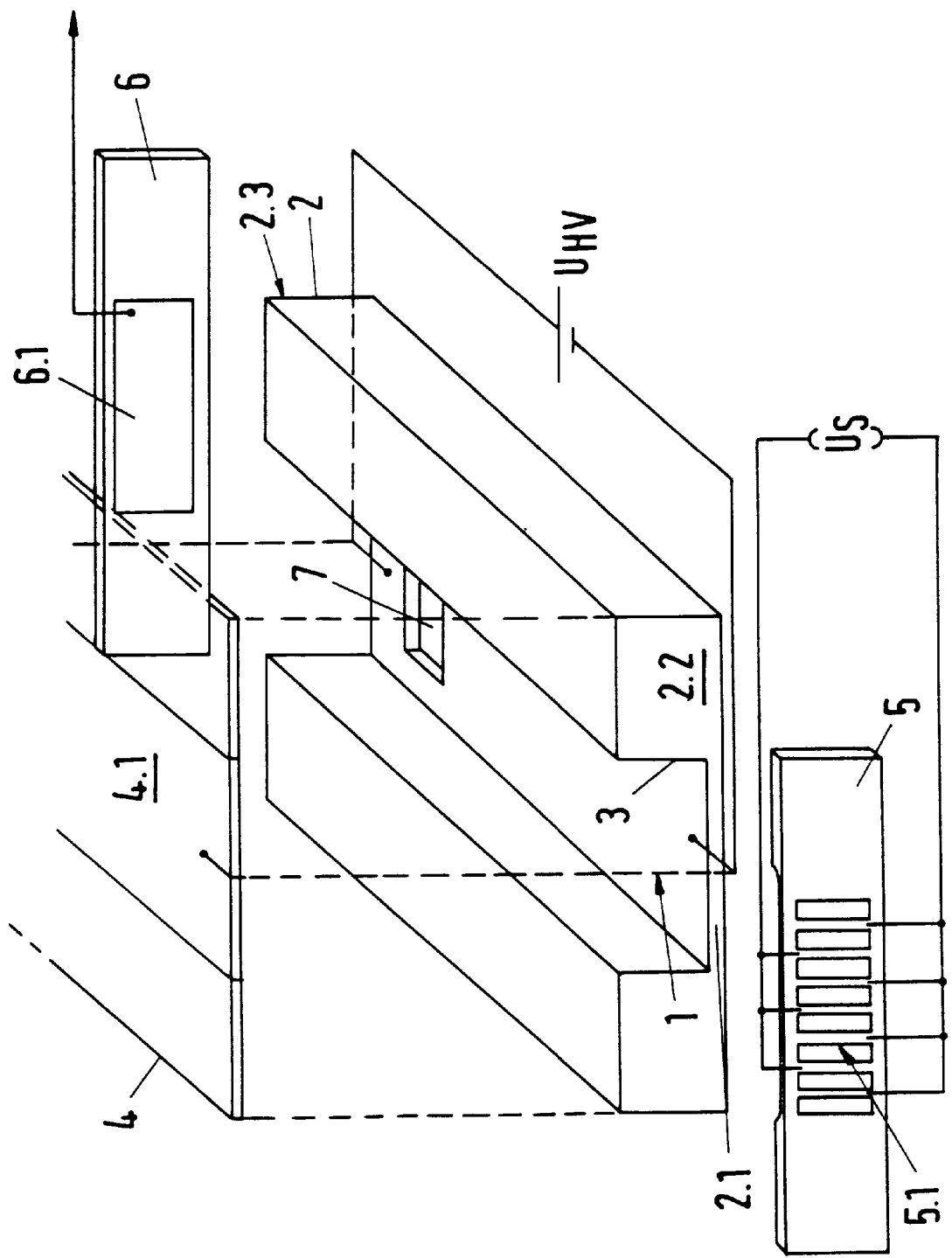

ION MOBILITY SPECTROMETER

BACKGROUND AND SUMMARY OF THE INVENTION

This application claims the priority of German patent document 196 50 612.3, the disclosure of which is expressly incorporated by reference herein.

The invention relates to an ion mobility spectrometer with an ion gate, a drift chamber, and an ion collector.

An ion mobility spectrometer of this generic type is described for example in European patent document EP 0 046 699 and in U.S. Pat. No. 4,390,784. It is essentially based on the fact that ions migrate to the ion collector in the drift chamber under the influence of an electrostatic field. The drift time is different for different ions and is determined by their mobility. The known ion mobility spectrometer has a drift chamber cross section of several square centimeters and drift distances up to 40 cm. The dimensions and high price of such devices limit the type and number of applications that lend themselves to this measurement method.

Attempts therefore have been made to miniaturize ion mobility spectrometers (International Journal of Environmental Analytical Chemistry, 1993, Volume 52, pages 189–193). Implementation of the concept described therein however has proven to be difficult or impossible, since the requirements for the individual components can be met only with difficulty if at all. No mention is made in the above article of the technical implementation of a miniaturized ion gate.

Hence, the object of the present invention is to provide an ion mobility spectrometer that can be miniaturized, and which can be manufactured using conventional methods, especially those known from semiconductor manufacturing.

Another object of the invention is to provide an ion mobility spectrometer which is small and less expensive to manufacture than known prior art devices.

These and other objects and advantages are achieved by an ion mobility spectrometer (IMS) according to the invention, in which the essential parts, namely the ion gate, the drift chamber, and the ion collector, consist of pieces that are essentially slice or wafer shaped, which are either anisotropically etchable or can be machined using micromechanical methods, and are held together by clamps, adhesives, or other assembly methods that are known of themselves. In the simplest form, the drift chamber consists of two sliced pieces with a through groove being etched or milled in one of them. The groove is covered by the other smooth piece so that a drift channel is produced. The drift channel is closed at one end by a grid-shaped ion gate, which is similarly made from a sliced piece by etching or milling, while the opposite end of the drift channel is closed by the ion collector, which is likewise made from a sliced piece that is electrically conducting on the inside.

In this manner, an IMS can be produced with a drift chamber cross section of less than 1 cm and a length of approximately 4 cm; in other words dimensions that correspond to about 1/10 of the previously conventional device measurements. The ionization chamber, which directly abuts the ion gate, can also be made in the same fashion.

Because of the small dimensions of the drift chamber, the measurement pulses are nearly delta-shaped with proper control of the ion gate, so that a detection limit for specific ions in the ppm range can be set. The power draw of the device can therefore be kept below 2 watts.

Because of its miniaturization, its low energy demand, and its low cost, the IMS can be used for drug or dangerous substance detection in the field, and can also be used for example as a monitoring device on high-voltage switches, which are filled with a protective gas (sulfur hexafluoride), whose concentration must be constantly monitored. Thus, frequent changing of the protective gas can therefore be eliminated.

Other objects, advantages and novel features of the present invention will become apparent from the following detailed description of the invention when considered in conjunction with the accompanying drawings.

BRIEF DESCRIPTION OF THE DRAWINGS

The single FIGURE of the drawing shows an exploded view of an embodiment of the invention, partially in schematic form.

DETAILED DESCRIPTION OF THE DRAWINGS

The Figure shows the structure of a drift chamber for an IMS according to the invention. Drift channel 1 is formed essentially by a silicon slice 2 about 1 mm thick and 40 mm long, in which slice a groove 3 has been etched or milled in such fashion that a layer with a thickness of approximately 20 $\mu$m is obtained that forms the lower side wall 2.1 of drift channel 1 of silicon slice 2. The upper side wall of drift channel 1 is formed by a cover plate 4 made of silicon which is glued flush on the remaining surfaces of slice 2. The front of drift chamber 1 is closed by a silicon slice 5 into which a gas-permeable grid 5.1 is etched in the vicinity of the drift chamber, with the individual grid rods being electrically conducting, by metallization for example, and with each rod being connected actively to the next grid rod but one. This silicon slice 5 forms the ion gate, and is glued to end 2.2 of silicon disk 2.

The back of drift chamber 1 is sealed by a silicon slice 6 which is likewise electrically conducting in the vicinity of the drift channel and serves as an ion collector. This silicon slice 6 is glued to end 2.3 of silicon disk 2.

In the bottom 2.1 of silicon slice 2, in the vicinity of ion collector 6, an opening 7 is etched that serves as a throughput opening for the drift gas.

To produce a drift field that is as disturbance-free and homogeneous as possible, both the bottom 2.1 of the silicon slice 2 and the portion 4.1 of silicon slice 4 that forms the cover of the drift chamber are provided with a high-ohmage resistance layer. The latter layers preferably are applied to the outside walls of the materials in order to avoid chemical influences on the ions, caused by the drift gas. Instead of resistance layers that have been applied, the silicon slices can also be doped in order to acquire the electrical conductivity that they require for developing a field in areas 2.1 and 4.1. The drift field is then produced by an external voltage $U_{HV}$ of approximately 2000 V, applied to the ends of the conducting layers of 2.1 and 4.1.

The drift gas can flow in drift chamber 1, depending on the requirements, either from opening 7 at ion gate 4, through grid rods 5.1, or in the opposite direction. The ions of the sample to be measured are generated in an ionization chamber (not shown) that can have essentially the same miniaturized design as the drift chamber and is placed on the front of ion gate 5. Grid 5.1 of ion gate 5 is controlled by a voltage Us in known fashion. That is, when a potential is applied between adjacent grid rods, the ion gate is blocked; and when no potential is applied, the ion gate is permeable to the ions from the ionization chamber. In the latter case, the ions are accelerated in the drift channel by the field of voltage $U_{HV}$ toward ion collector 6, where they strike collecting plate 6.1 and generate an electrical signal there, which is evaluated in known fashion.

To create a uniform flow of the drift gas it is advantageous for throughout opening 7 to have a cross section that corresponds roughly to the cross section of drift channel 1 through which flow occurs.

It is possible to achieve a larger drift channel cross section; for example, by using in place of a plane cover plate 4, a part that is symmetrical with respect to silicon slice 2, and has a groove with the same dimension. The silicon slices 5 and 6 of the ion gate and/or ion collector are then enlarged accordingly, so that they cover drift channel 1, which is then twice as high.

Instead of silicon, of course, other materials that are either anisotropically etchable or can be machined by micromechanical means, for example gallium arsenide, glass, and the like, can be used for the components of the drift chamber.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. An ion mobility spectrometer having an ion gate, a drift chamber, and an ion collector, wherein:
   the ion gate comprises a slice shaped anisotropically etchable first piece;
   the drift chamber comprises at least two slice-shaped second pieces, said pieces forming side walls, and at least one of said pieces having a gas throughput opening;
   the ion collector comprises a slice-shaped third piece; and
   the ion gate and ion collector are located on opposite ends of the drift chamber.

2. The ion mobility spectrometer according to claim 1 wherein:
   at least one of said at least two second pieces comprises a slice-shaped body with at least two opposite planar faces and at least one planar lateral surface; and
   a through groove extends in that face of the slice-shaped piece from one face to the other.

3. The ion mobility spectrometer according to claim 1 wherein the ion gate is made as a gas-permeable grid with electrically conducting grid rods located side-by-side and parallel to one another, each grid rod being insulated electrically from an immediately adjacent grid rod.

4. The ion mobility spectrometer according to claim 3 wherein each grid rod is connected electrically with each second consecutive grid rod.

5. The ion mobility spectrometer according to claim 1 wherein an ionization chamber is located on a side of the ion gate that is opposite the drift chamber, said ionization chamber being formed by at least two slice-shaped pieces.

6. The ion mobility spectrometer according to claim 1 wherein a uniform resistance layer in the form of conducting strips is located on at least two opposite lateral inside walls of the drift chamber, said strip conductors being connected with one another by a stepped resistance chain.

7. The ion mobility spectrometer according to claim 1 wherein an area of the gas throughput opening is equal to a cross-sectional area of the drift chamber.

8. The ion mobility spectrometer according to claim 1 wherein at least one of the ion gate, the drift chamber, or the ion collector is made of a material selected from the group consisting of monocrystalline silicon and gallium arsenide.

9. An ion mobility spectrometer comprising:
   a first slice-shaped piece of material;
   a second slice-shaped piece of material, at least one of said first and second slice-shaped pieces having a longitudinal groove therein, said first and second pieces being layered together, forming an enclosed longitudinal drift chamber having a gas throughput opening formed therein;
   an ion gate comprising a slice-shaped piece of material disposed at a first end of said drift chamber;
   an ion collector comprising a slice shaped piece of material disposed at a second end of said drift chamber opposite said first end;
   a first voltage source connected to apply an electric field to said drift chamber; and
   a second voltage source connected to apply a voltage to said ion gate;
   wherein said slice-shaped pieces are made of a material which is one of anisotropically etchable and machinable by means of micromechanical methods.

10. An ion mobility spectrometer comprising components made of semiconductor material, and having an ion gate, a drift chamber and an ion collector, with the ion gate and the ion collector disposed at opposite ends of the drift chamber, wherein:
    the ion gate comprises a gas permeable gate having a plurality of electrically conducting parallel grid rods, each grid rod being electrically insulated from immediately adjacent grid rods and electrically connected to alternate grid rods beyond the immediately adjacent grid rods;
    the grid rods are made of a slice-shaped anisotropically etchable first piece of semiconductor material;
    the drift chamber is made of at least two stacked slice-shaped second pieces of semiconductor material, at least one of which has a gas passageway in the form of a longitudinal groove formed therein, with an opening through a wall at one end thereof, said groove having surfaces which cooperate with a surface of the other of said at least two second pieces to form walls of said passageway;
    uniform resistive elements are formed on at least two opposite walls of said passageway and connected with each other by a stepped resistance chain; and
    means for applying a first voltage to said grid rods and a second voltage to said resistive elements.

11. An ion mobility spectrometer according to claim 10 wherein said resistive element comprise resistance layers.

12. An ion mobility spectrometer according to claim 10 wherein said resistive elements comprise step shaped conducting traces.

13. An ion mobility spectrometer according to claim 10 wherein the drift chamber comprises a slice-shaped body having at least one flat side surface with said groove formed continuously therein and at least two flat ends disposed at opposite ends of the groove.

14. An ion mobility spectrometer according to claim 13, further comprising an ionization chamber situated adjacent the ion gate opposite the drift chamber, said ionization chamber being made of at least two slice-shaped pieces.

* * * * *